US010716522B2

(12) United States Patent
Sato et al.

(10) Patent No.: US 10,716,522 B2
(45) Date of Patent: Jul. 21, 2020

(54) RADIATION IMAGE CAPTURING APPARATUS, RADIATION IMAGE CAPTURING SYSTEM, AND METHOD OF CONTROLLING RADIATION IMAGE CAPTURING APPARATUS

(71) Applicant: CANON KABUSHIKI KAISHA, Tokyo (JP)

(72) Inventors: Eriko Sato, Tokyo (JP); Tomoyuki Yagi, Chofu (JP); Shinichi Takeda, Kawasaki (JP); Hideyuki Okada, Honjo (JP); Takuya Ryu, Kokubunji (JP); Katsuro Takenaka, Honjo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 16/150,523

(22) Filed: Oct. 3, 2018

(65) Prior Publication Data

US 2019/0029618 A1 Jan. 31, 2019

Related U.S. Application Data

(63) Continuation of application No. PCT/JP2017/004864, filed on Feb. 10, 2017.

(30) Foreign Application Priority Data

Apr. 18, 2016 (JP) ................................. 2016-083124

(51) Int. Cl.
A61B 6/00 (2006.01)
H04N 5/353 (2011.01)
(Continued)

(52) U.S. Cl.
CPC .......... A61B 6/4266 (2013.01); A61B 6/4233 (2013.01); A61B 6/542 (2013.01);
(Continued)

(58) Field of Classification Search
CPC .......... H04N 5/32; H04N 5/325; H04N 5/353; H04N 5/3696; A61B 6/4233; A61B 6/542; A61B 6/4266; G01T 7/00; G01T 7/02
(Continued)

(56) References Cited

U.S. PATENT DOCUMENTS 6,690,493 B1 * 2/2004 Kobayashi ........... H04N 5/3454
348/307
7,227,926 B2 6/2007 Kameshima et al.
(Continued)

FOREIGN PATENT DOCUMENTS

JP 2010075556 A 4/2010
JP 2012119770 A 6/2012
(Continued)

Primary Examiner — Blake C Riddick
(74) Attorney, Agent, or Firm — Venable LLP

(57) ABSTRACT

A radiation image capturing apparatus is provided. The radiation image capturing apparatus includes an image capturing unit configured to capture a radiation image. The image capturing unit includes a detection element configured to detect radiation. The radiation image capturing apparatus comprises a processor configured to perform, in accordance with an exposure request from a user, a first reset operation of resetting the detection element, and configured to detect an amount of irradiation of the radiation based on a signal from the detection element after the first reset operation.

13 Claims, 9 Drawing Sheets

(51) Int. Cl.
*H04N 5/32* (2006.01)
*H04N 5/369* (2011.01)
*G01T 7/02* (2006.01)
*H04N 5/325* (2006.01)

(52) U.S. Cl.
CPC ............... *G01T 7/02* (2013.01); *H04N 5/32* (2013.01); *H04N 5/325* (2013.01); *H04N 5/353* (2013.01); *H04N 5/3696* (2013.01)

(58) Field of Classification Search
USPC ............ 378/62; 250/370.08, 370.09, 370.11
See application file for complete search history.

(56) References Cited

U.S. PATENT DOCUMENTS

| | | | |
|---|---|---|---|
| 7,256,404 B2 | 8/2007 | Inoue et al. |
| 7,342,221 B2 | 3/2008 | Takenaka et al. |
| 7,381,963 B2 | 6/2008 | Endo et al. |
| 7,386,089 B2 | 6/2008 | Endo et al. |
| 7,391,029 B2 | 6/2008 | Takeda et al. |
| 7,403,594 B2 | 7/2008 | Endo et al. |
| 7,442,939 B2 | 10/2008 | Yagi et al. |
| 7,470,911 B2 | 12/2008 | Yagi |
| 7,514,663 B2 | 4/2009 | Yagi et al. |
| 7,514,686 B2 | 4/2009 | Ogawa et al. |
| 7,532,706 B2 | 5/2009 | Kameshima et al. |
| 7,541,591 B2 | 6/2009 | Endo et al. |
| 7,573,038 B2 | 8/2009 | Yokoyama et al. |
| 7,573,041 B2 | 8/2009 | Kameshima et al. |
| 7,595,493 B2 | 9/2009 | Okada et al. |
| 7,613,277 B2 | 11/2009 | Takenaka et al. |
| 7,683,337 B2 | 3/2010 | Yagi et al. |
| 7,714,294 B2 | 5/2010 | Sawada et al. |
| 7,718,973 B2 | 5/2010 | Endo et al. |
| 7,723,693 B2 | 5/2010 | Okada et al. |
| 7,724,874 B2 | 5/2010 | Kameshima et al. |
| 7,732,776 B2 | 6/2010 | Takenaka et al. |
| 7,750,309 B2 | 7/2010 | Endo et al. |
| 7,777,167 B2 | 8/2010 | Takeda et al. |
| 7,786,448 B2 | 8/2010 | Endo et al. |
| 7,791,035 B2 | 9/2010 | Yokoyama et al. |
| 7,847,263 B2 | 12/2010 | Yagi et al. |
| 7,850,367 B2 | 12/2010 | Takenaka et al. |
| 7,869,568 B2 | 1/2011 | Yokoyama et al. |
| 7,872,218 B2 | 1/2011 | Endo et al. |
| 7,880,145 B2 | 2/2011 | Yagi et al. |
| 7,952,058 B2 | 5/2011 | Nomura et al. |
| 7,965,817 B2 | 6/2011 | Kameshima et al. |
| 7,994,481 B2 | 8/2011 | Yagi et al. |
| 8,093,562 B2 | 1/2012 | Yokoyama et al. |
| 8,107,588 B2 | 1/2012 | Kameshima et al. |
| 8,115,177 B2 | 2/2012 | Takeda et al. |
| 8,222,611 B2 | 7/2012 | Yagi et al. |
| 8,247,779 B2 | 8/2012 | Kameshima et al. |
| 8,304,735 B2 | 11/2012 | Inoue et al. |
| 8,440,975 B2 | 5/2013 | Inoue et al. |
| 8,576,294 B2 | 11/2013 | Kameshima et al. |
| 8,653,463 B2 | 2/2014 | Sawada et al. |
| 8,723,996 B2 | 5/2014 | Yokoyama et al. |
| 8,792,024 B2 | 7/2014 | Takenaka et al. |
| 8,809,795 B2 | 8/2014 | Takenaka et al. |
| 8,829,438 B2 | 9/2014 | Sato et al. |
| 8,952,332 B2 | 2/2015 | Uchiyama |
| 9,048,154 B2 | 6/2015 | Takenaka et al. |
| 9,081,104 B2 | 7/2015 | Sawada et al. |
| 9,128,196 B2 | 9/2015 | Sato et al. |
| 9,134,432 B2 | 9/2015 | Iwashita et al. |
| 9,234,966 B2 | 1/2016 | Sugawara et al. |
| 9,354,333 B2 | 5/2016 | Inoue et al. |
| 9,366,767 B2 | 6/2016 | Inoue et al. |
| 9,423,512 B2 | 8/2016 | Sato et al. |
| 9,445,030 B2 | 9/2016 | Yagi et al. |
| 9,462,989 B2 | 10/2016 | Takenaka et al. |
| 9,468,414 B2 | 10/2016 | Ryu et al. |
| 9,470,800 B2 | 10/2016 | Iwashita et al. |
| 9,470,802 B2 | 10/2016 | Okada et al. |
| 9,541,653 B2 | 1/2017 | Iwashita et al. |
| 9,655,586 B2 | 5/2017 | Yagi et al. |
| 9,737,271 B2 | 8/2017 | Iwashita et al. |
| 9,812,474 B2 | 11/2017 | Yagi et al. |
| 9,885,790 B2 | 2/2018 | Okada et al. |
| 9,971,046 B2 | 5/2018 | Ryu et al. |
| 9,980,685 B2 | 5/2018 | Iwashita et al. |
| 9,989,656 B2 | 6/2018 | Sato et al. |
| 10,009,990 B2 | 6/2018 | Takenaka et al. |
| 2010/0148080 A1 | 6/2010 | Endo et al. |
| 2010/0191107 A1* | 7/2010 | Bowers ............... A61B 5/0091 600/436 |
| 2011/0286575 A1* | 11/2011 | Omernick ............... A61B 6/42 378/62 |
| 2011/0317054 A1 | 12/2011 | Kameshima et al. |
| 2012/0132810 A1* | 5/2012 | Uchiyama ............... H04N 5/32 250/358.1 |
| 2013/0161526 A1* | 6/2013 | Tajima ................ A61B 6/5258 250/394 |
| 2013/0187054 A1 | 7/2013 | Ishii et al. |
| 2013/0221198 A1 | 8/2013 | Sawada et al. |
| 2013/0322597 A1* | 12/2013 | Uchiyama ................ G01T 1/17 378/62 |
| 2014/0023181 A1* | 1/2014 | Noshi ................ A61B 6/4241 378/98 |
| 2014/0034836 A1 | 2/2014 | Takei et al. |
| 2014/0239186 A1 | 8/2014 | Sato et al. |
| 2014/0361189 A1 | 12/2014 | Kameshima et al. |
| 2015/0192684 A1 | 7/2015 | Ito |
| 2016/0021290 A1* | 1/2016 | Yagi ..................... H04N 5/378 250/394 |
| 2016/0270755 A1 | 9/2016 | Takenaka et al. |
| 2017/0285189 A1 | 10/2017 | Ryu et al. |
| 2018/0063933 A1 | 3/2018 | Okada et al. |
| 2018/0070906 A1 | 3/2018 | Terui et al. |
| 2018/0128755 A1 | 5/2018 | Iwashita et al. |
| 2018/0129120 A1 | 5/2018 | Sato et al. |
| 2018/0136343 A1 | 5/2018 | Terui et al. |
| 2018/0216993 A1 | 8/2018 | Okada |
| 2018/0295294 A1 | 10/2018 | Kameshima et al. |

FOREIGN PATENT DOCUMENTS

| | | |
|---|---|---|
| JP | 2014-071034 | 4/2014 |
| JP | 2016025465 A | 2/2016 |

* cited by examiner

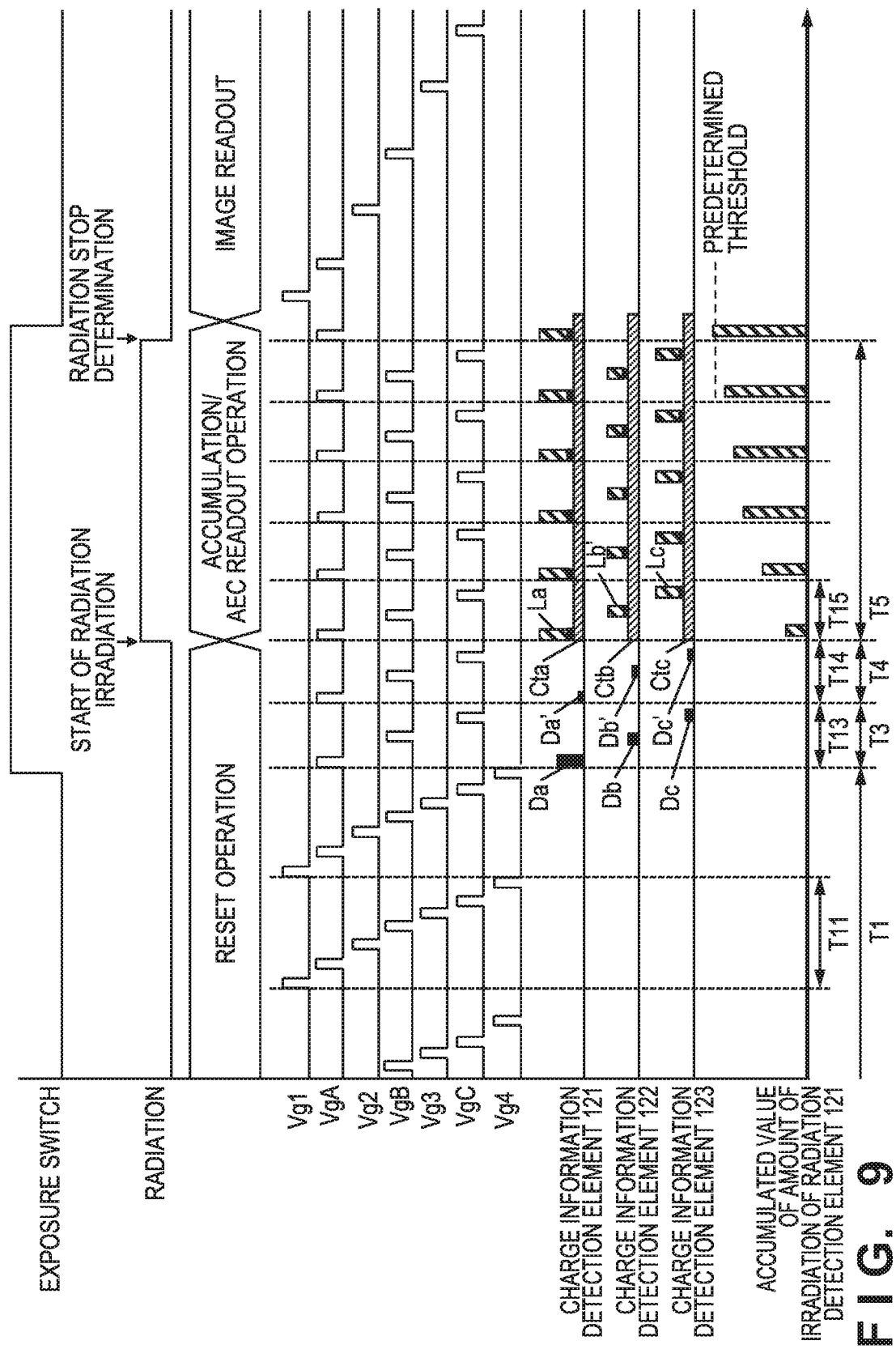

RADIATION IMAGE CAPTURING APPARATUS, RADIATION IMAGE CAPTURING SYSTEM, AND METHOD OF CONTROLLING RADIATION IMAGE CAPTURING APPARATUS

CROSS-REFERENCE TO RELATED APPLICATIONS

This application is a Continuation of International Patent Application No. PCT/JP2017/004864, filed Feb. 10, 2017, which claims the benefit of Japanese Patent Application No. 2016-083124, filed Apr. 18, 2016, both of which are hereby incorporated by reference herein in their entirety.

BACKGROUND OF THE INVENTION

Field of the Invention

The present invention relates to a radiation image capturing apparatus, a radiation image capturing system, and a method of controlling the radiation image capturing apparatus.

Description of the Related Art

A radiation image capturing apparatus that includes a flat panel detector (FPD) where pixels each obtained by combining a conversion element which converts radiation into charges and a switch element such as a thin film transistor (TFT) are arranged in an array is widely used. In such a radiation image capturing apparatus, an Automatic Exposure Control (AEC) function is known. The AEC function detects the amount of irradiation of radiation entering the radiation image capturing apparatus during radiation irradiation. Japanese Patent Laid-Open No. 2010-75556 describes a radiation image capturing apparatus that turns on (electrically connects) a switch element of a pixel selected among a plurality of pixels to detect the amount of irradiation from the start of radiation irradiation and stops radiation irradiation if an accumulated value of a signal output from this pixel exceeds a set threshold.

SUMMARY OF THE INVENTION

In a conventional radiation image capturing apparatus, before capturing a radiation image, a reset operation of resetting each pixel repeatedly in a predetermined cycle is performed in order to remove charges generated by a dark current in each pixel arranged in the radiation image capturing apparatus. During the reset operation, all the pixels are reset sequentially for each row. When shifting to a readout operation immediately in accordance with a radiation irradiation instruction as described in Japanese Patent Laid-Open No. 2010-75556, a time from last resetting to the first signal readout for detecting the amount of irradiation may vary in a pixel that detects the selected amount of irradiation. If the time from resetting to the readout operation varies, the readout amount of charges may vary due to a variation in amount of the charges owing to the dark current, decreasing the accuracy of the detected amount of irradiation of radiation.

Some embodiments of the present invention provide a technique of more accurately detecting the amount of irradiation of radiation entering the radiation image capturing apparatus.

According to some embodiments, a radiation image capturing apparatus including an image capturing unit configured to capture a radiation image, wherein, the image capturing unit includes a detection element configured to detect radiation, and the radiation image capturing apparatus comprises a processor configured to perform, in accordance with an exposure request from a user, a first reset operation of resetting the detection element, and configured to detect an amount of irradiation of the radiation based on a signal from the detection element after the first reset operation, is provided.

According to some other embodiments, a control method for controlling a radiation image capturing apparatus including an image capturing unit configured to capture a radiation image, wherein, the image capturing unit includes a detection element configured to detect radiation, and the method comprises resetting the detection element in accordance with an exposure request from a user; and detecting an amount of irradiation of the radiation based on a signal from the detection element after the resetting, is provided.

Further features of the present invention will become apparent from the following description of exemplary embodiments with reference to the attached drawings.

BRIEF DESCRIPTION OF THE DRAWINGS

The accompanying drawings, which are incorporated in and constitute a part of the specification, illustrate embodiments of the invention and, together with the description, serve to explain the principles of the invention.

FIG. 9 is a timing chart showing the driving method of the radiation image capturing system in FIG. 1.

DESCRIPTION OF THE EMBODIMENTS

A detailed embodiment of a radiation image capturing apparatus according to the present invention will be described below with reference to the accompanying drawings. Note that radiation according to the present invention can include not only α-rays, β-rays, and γ-rays that are beams generated by particles (including photons) emitted by radioactive decay but also beams having energy equal to or higher than the energy of the above beams generated by the particles, for example, X-rays, particle beams, and cosmic rays.

Figure 1:
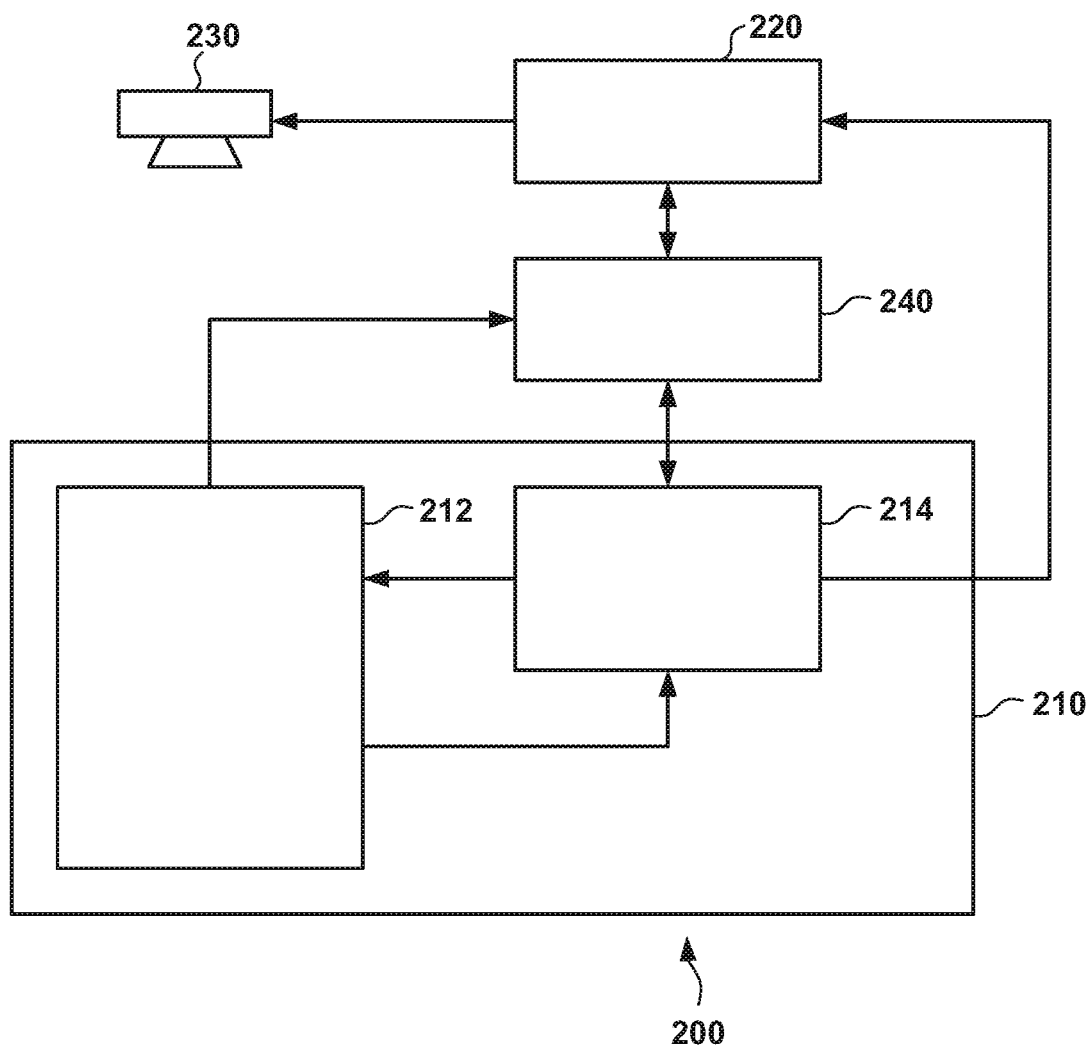
FIG. 1 is a diagram showing an example of the arrangement of a radiation image capturing system using a radiation image capturing apparatus according to an embodiment of the present invention.

The arrangements and operations of the radiation image capturing apparatus and a radiation image capturing system according to an embodiment of the present invention will be described with reference to FIGS. 1 to 9. FIG. 1 is a diagram showing an example of the arrangement of a radiation image capturing system 200 using a radiation image capturing apparatus 210 according to an embodiment of the present invention. The radiation image capturing system 200 is configured to electrically capture an optical image formed by radiation and obtain an electrical radiation image (that is, radiation image data).

The radiation image capturing system 200 includes the radiation image capturing apparatus 210, an irradiation controller 220, a radiation source 230, and a computer 240. The radiation source 230 performs radiation irradiation in accordance with an irradiation instruction from the irradiation controller 220. Radiation emitted from the radiation source 230 passes through an object (not shown) and irradiates the radiation image capturing apparatus 210. The radiation source 230 stops radiation irradiation in accordance with an irradiation stop instruction from the irradiation controller 220.

The radiation image capturing apparatus 210 includes an image capturing unit 212 configured to capture a radiation image and a processor 214 configured to detect the amount of irradiation of incident radiation. The image capturing unit 212 includes a pixel array where a plurality of pixels for capturing a radiation image and detection elements for detecting the amounts of irradiation of radiation are arranged. Based on a signal output from the image capturing unit 212, the processor 214 detects the amount of the incident radiation and outputs an irradiation stop signal for stopping radiation irradiation from the radiation source 230. The irradiation stop signal is supplied to the irradiation controller 220, and the irradiation controller 220 sends the irradiation stop instruction to the radiation source 230 in accordance with the irradiation stop signal. In this embodiment, the processor 214 also controls the operation of the image capturing unit 212. The processor 214 may be formed by, for example, a PLD (Programmable Logic Device) such as an FPGA (Field Programmable Gate Array). Alternatively, the processor 214 may be formed by an ASIC (Application Specific Integrated Circuit) or a general-purpose computer with a program installed therein. Alternatively, the processor 214 may be formed by a combination of all or some of them. The operation of the image capturing unit 212 is not limited to control by the processor 214, and a controller configured to control the operation of the image capturing unit 212 may be arranged separately from the processor. In this case, the controller arranged separately may be formed by, for example, a PLD such as an FPGA or an ASIC.

The computer 240 controls the radiation image capturing apparatus 210 and the irradiation controller 220. The computer 240 also receives the radiation image data output from radiation image capturing apparatus 210 and processes the radiation image data. In an example, the irradiation controller 220 includes an exposure switch, and sends an irradiation instruction to the radiation source 230 and sends a start notification indicating the start of radiation irradiation to the computer 240 when a user turns on the exposure switch. The computer 240 receiving the start notification notifies, in accordance with the start notification, the processor 214 in the radiation image capturing apparatus 210 of the start of radiation irradiation.

Figure 2:
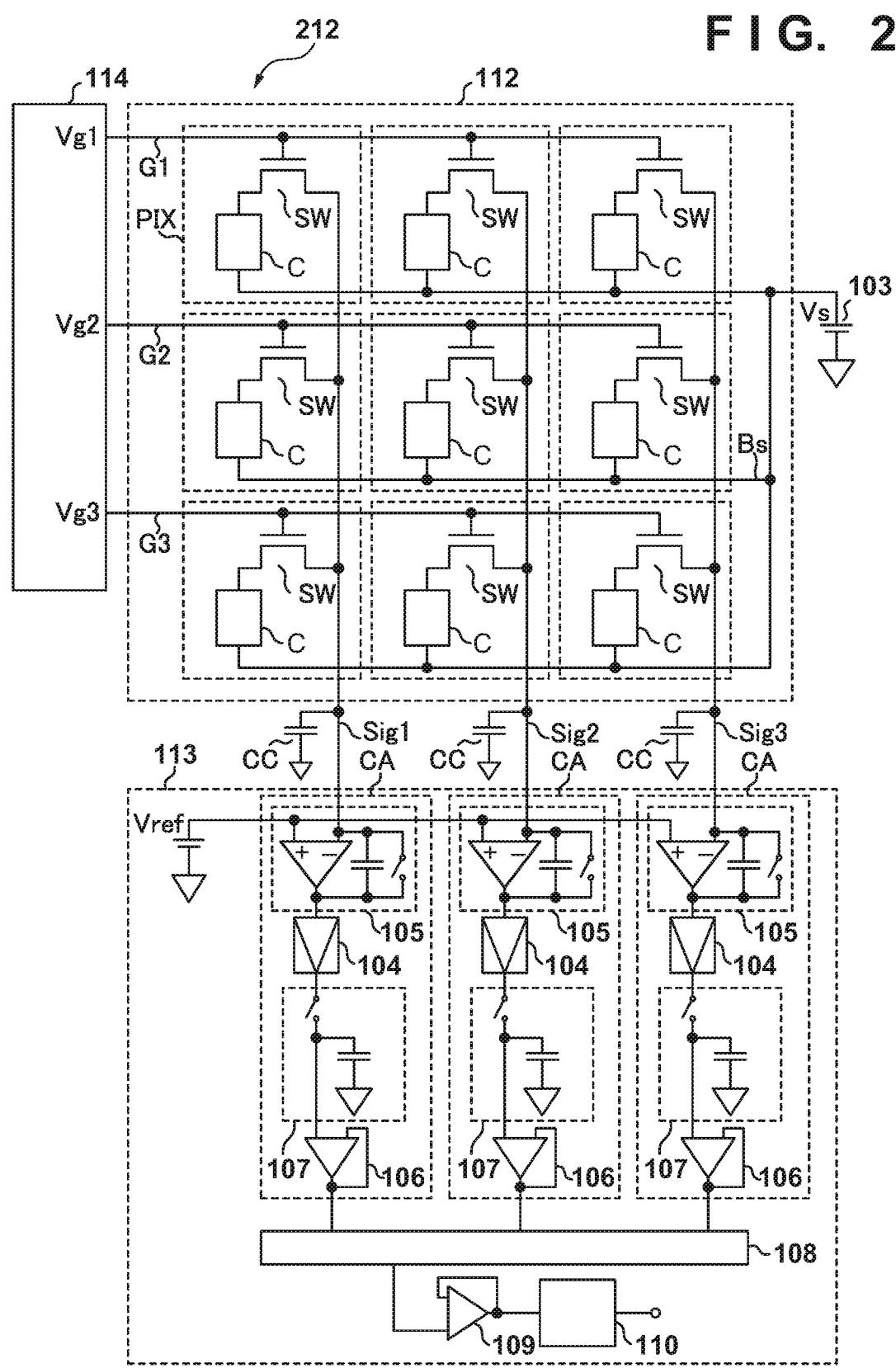
FIG. 2 is a diagram showing an example of the arrangement of a detector of the radiation image capturing apparatus in FIG. 1.

FIG. 2 shows an example of the arrangement of the image capturing unit 212 in the radiation image capturing apparatus 210. The image capturing unit 212 includes a pixel array 112 that includes a plurality of pixels PIX for capturing a radiation image. The image capturing unit 212 also includes a driver (row selecting circuit) 114 configured to drive the pixel array 112 and a readout unit 113 configured to detect signals from the pixels PIX. The image capturing unit 212 also includes gate lines G for transmitting driving signals from the driver 114 by the respective pixels PIX and column signal lines Sig for transmitting signals output from the respective pixels PIX to the readout unit 113. In FIG. 2, the 3 (rows)×3 (columns) pixels PIX are arranged in the pixel array 112 for the sake of descriptive convenience. In practice, however, more pixels PIX can be arranged in the pixel array 112. For example, the 17-inch pixel array 112 can include about the 3,000 (rows)×3,000 (columns) pixels PIX.

Each pixel PIX includes a conversion element C that detects radiation and a switch SW that connects the conversion element C and a corresponding one of the column signal lines Sig. The conversion element C outputs an electrical signal (charges) corresponding to the amount of radiation entering the conversion element C to the column signal line Sig via the switch SW. The conversion element C may be formed as a conversion element of a direct type that converts radiation into an electrical signal directly or may be formed as a conversion element of an indirect type that detects, after radiation is converted into light, the converted light. For the conversion element C of the indirect type, a scintillator for converting radiation into light can be shared by the plurality of pixels PIX.

The switch SW can be formed by, for example, a transistor such as a thin film transistor (TFT) that includes a control terminal (gate) and two main terminals (the source and the drain). The conversion element C includes two main electrodes, the one main electrode of the conversion element C is connected to the one main terminal out of the two main terminals of the switch SW, and the other main electrode of the conversion element C is connected to a bias power supply 103 via a common bias line Bs. The bias power supply 103 supplies a bias voltage Vs to the respective conversion elements C. The control terminals of the switches SW in the pixels PIX of the first row are connected to a gate line G1. The control terminals of the switches SW in the pixels PIX of the second row are connected to a gate line G2. The control terminals of the switches SW in the pixels PIX of the third row are connected to a gate line G3. The driver 114 supplies respective driving signals Vg1, Vg2, and Vg3 to the gate lines G1, G2, and G3.

The main terminals out of the main terminals of the switches SW in the pixels PIX of the first column which are not connected to the conversion elements C are connected to a column signal line Sig1 of the first column. The main terminals of the switches SW in the pixels PIX of the second column which are not connected to the conversion elements C are connected to a column signal line Sig2 of the second column. The main terminals of the switches SW in the pixels PIX of the third column which are not connected to the conversion elements C are connected to a column signal line Sig3 of the third column. Each column signal line Sig includes a capacitor CC.

The readout unit 113 includes a plurality of column amplifying units CA so that one column amplifying unit CA corresponds to one column signal line Sig. Each column amplifying unit CA can include an integration amplifier 105, a variable amplifier 104, a sample and hold circuit 107, and a buffer circuit 106. The integration amplifier 105 amplifies each signal that appears in the corresponding signal line Sig. The integration amplifier 105 can include an operational amplifier, an integration capacitor connected in parallel between the inverting input terminal and the output terminal of the operational amplifier, and a reset switch. A reference potential Vref is supplied to the non-inverting input terminal of the operational amplifier. The potential of each column signal line Sig is reset to the reference potential Vref together with the resetting of the integration capacitor by turning on the reset switch. The reset switch can be controlled by a reset pulse supplied from the processor 214.

The variable amplifier 104 amplifies a signal by an amplification factor set by the integration amplifier 105. The sample and hold circuit 107 samples and holds the signal output from the variable amplifier 104. The sample and hold circuit 107 can be constituted by, for example, a sampling switch and a sampling capacitor. The buffer circuit 106 buffers (impedance-converts) the signal output from the sample and hold circuit 107 and outputs the signal. The sampling switch can be controlled by a sampling pulse supplied from the processor 214.

The readout unit 113 also includes a multiplexer 108 that selects and outputs, in a predetermined order, the signals from the plurality of column amplifying units CA provided so as to correspond with the plurality of column signal lines Sig, respectively. The multiplexer 108 includes, for example, a shift register. The shift register performs a shift operation in accordance with a clock signal supplied from the processor 214. The shift register selects a signal out of the plurality of column amplifying units CA. The readout unit 113 can also include a buffer 109 which buffers (impedance-converts) the signal output from the multiplexer 108 and an AD convertor 110 which converts an analog signal, as the output signal from the buffer 109, into a digital signal. The output of the AD convertor 110, that is, the radiation image data is supplied to the computer 240.

Figure 3:
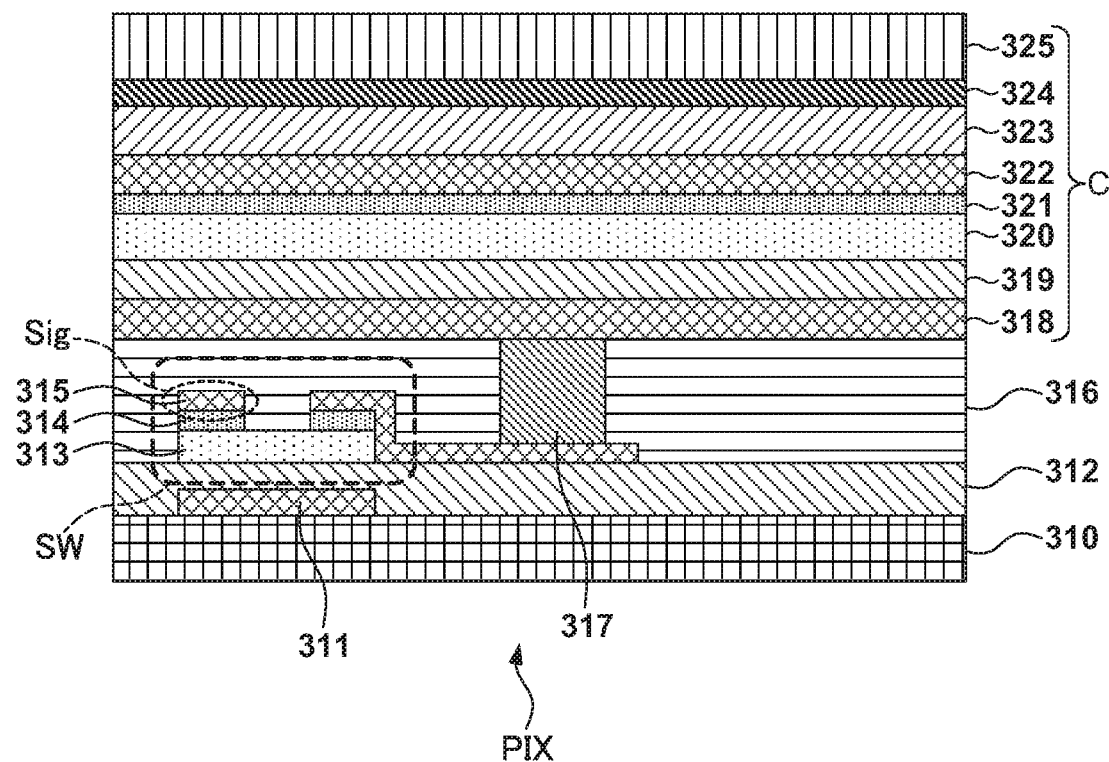
FIG. 3 is a sectional view showing a pixel of the radiation image capturing apparatus in FIG. 1.

FIG. 3 shows an example of the sectional structure of the pixel PIX including the conversion element C of the indirect type. The pixel PIX is formed on an insulating substrate 310 such as a glass substrate. Alternatively, for example, a metal or semiconductor substrate may be used for the substrate 310, and the pixel PIX may be formed on an insulating layer on the substrate. The pixel PIX includes, on the substrate 310, a conductive layer 311, an insulating layer 312, a semiconductor layer 313, impurity semiconductor layers 314, and conductive layers 315. The conductive layer 311 forms the gate of a transistor (for example, a TFT) that forms the switch SW. The insulating layer 312 is arranged so as to cover the conductive layer 311. The semiconductor layer 313 is arranged above a portion of the conductive layer 311 that forms the gate on the insulating layer 312. The impurity semiconductor layers 314 are arranged on the semiconductor layer 313 so as to form two main terminals (the source and the drain) of the transistor that forms the switch SW. The conductive layers 315 form wiring patterns connected to the two main terminals (the source and the drain) of the transistor that forms the switch SW. One part of the conductive layers 315 forms the column signal line Sig, and the other part forms a wiring pattern for connecting the conversion element C and the switch SW.

The pixel PIX further includes an interlayer dielectric film 316 that covers the insulating layer 312 and the conductive layers 315. The interlayer dielectric film 316 includes a contact plug 317 to be connected to the switch SW via the conductive layer 315. In the pixel PIX, the conversion element C is arranged on the interlayer dielectric film 316. In FIG. 3, the conversion element C is formed as a conversion element of an indirect type that includes a scintillator 325 for converting radiation into light. The conversion element C includes a conductive layer 318, an insulating layer 319, a semiconductor layer 320, an impurity semiconductor layer 321, a conductive layer 322, a protection layer 323, an adhesion layer 324, and the scintillator 325 stacked on the interlayer dielectric film 316.

The conductive layer 318 and the conductive layer 322, respectively, form a lower electrode and upper electrode of a photoelectric conversion element that forms the conversion element C. The conductive layer 322 is made of, for example, a transparent material. The conductive layer 318, the insulating layer 319, the semiconductor layer 320, the impurity semiconductor layer 321, and the conductive layer 322 form a MIS sensor serving as a photoelectric conversion element. The conversion element C is not limited to a MIS conversion element and may be, for example, a pn or pin photodiode. The impurity semiconductor layer 321 is formed by, for example, an n-type impurity semiconductor. The scintillator 325 is formed by, for example, a gadolinium-based material such as gadolinium oxysulfide (GOS) or a material such as cesium iodide (CsI).

Alternatively, the conversion element C may be formed as a conversion element of a direct type that converts incident radiation into an electrical signal (charges) directly. A conversion element that is mainly made of, for example, amorphous selenium (a-Se), gallium arsenide (GaAs), gallium phosphide (GaP), lead iodide (PbI), mercury iodide (HgI), cadmium telluride (CdTe), cadmium zinc telluride (CdZnTe), or the like can be given as the conversion element C of the direct type. In this case, the scintillator 325 need not be arranged.

In an arrangement shown in FIG. 3, in orthogonal projection to a surface where the pixel array 112 is formed, each column signal line Sig overlaps a part of a corresponding one of the pixels PIX. While such an arrangement is advantageous in increasing the area of the conversion element C in the pixel PIX, it is disadvantageous in increasing capacitive coupling between the column signal line Sig and the conversion element C. When radiation enters the conversion element C, charges are accumulated in the conversion element C, and the potential of the conductive layer 318 serving as the lower electrode changes, the potential of the column signal line Sig also changes by the capacitive coupling between the column signal line Sig and the conversion element C. An overlap between the pixel PIX and the column signal line Sig can be designed appropriately in accordance with specifications required of the radiation image capturing apparatus 210.

The operations of the radiation image capturing apparatus 210 and radiation image capturing system 200 will be described next with reference to FIGS. 4 to 9. The operation of the radiation image capturing system 200 is controlled by the computer 240. The operation of the radiation image capturing apparatus 210 is controlled by the processor 214 under the control by the computer 240.

Figure 4:
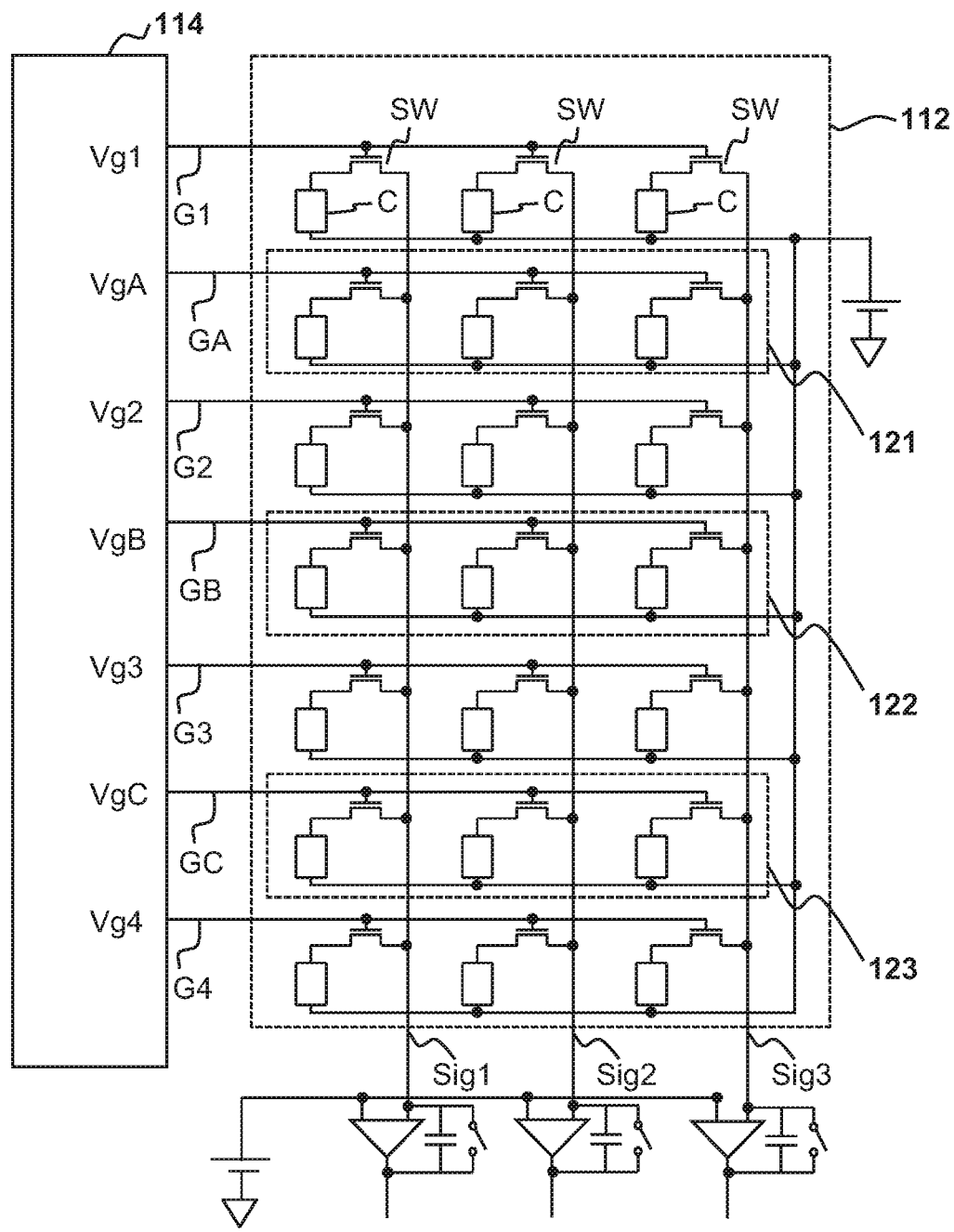
FIG. 4 is an equivalent circuit diagram of the radiation image capturing apparatus in FIG. 1.

FIG. 4 is a simple equivalent circuit diagram of the pixel array 112. In an arrangement shown in FIG. 4, the pixel array 112 includes the 3 (rows)×7 (columns) pixels PIX. In this embodiment, the pixels PIX out of the plurality of pixels PIX connected to gate lines GA, GB, and GC are used as detection elements 121, 122, and 123 each for detecting the amount of irradiation of incident radiation. In this embodiment, each of the detection elements 121, 122, and 123 can have the same structure as other pixels PIX and form a signal that forms radiation image data. By reading out a signal from each of the detection elements 121, 122, and 123 during radiation irradiation as well, it is possible to detect the amount of irradiation of the incident radiation and use it for, for example, the operation of Automatic Exposure Control (AEC). In the arrangement shown in FIG. 4, the detection elements are set for every other row out of the 3 (row)×7 (columns) pixels PIX. In practice, however, detection elements may be set for about one row in several hundred rows at a position capable of covering a lung field in accordance with, for example, imaging of a chest region. There may be only one detection element or a plurality of detection elements as shown in FIG. 4. In this embodiment, the detection elements use the pixels PIX selected from the plurality of pixels PIX. However, a dedicated detection element different from the pixel PIX may be used in order to detect the amount of irradiation of radiation.

Figure 5:
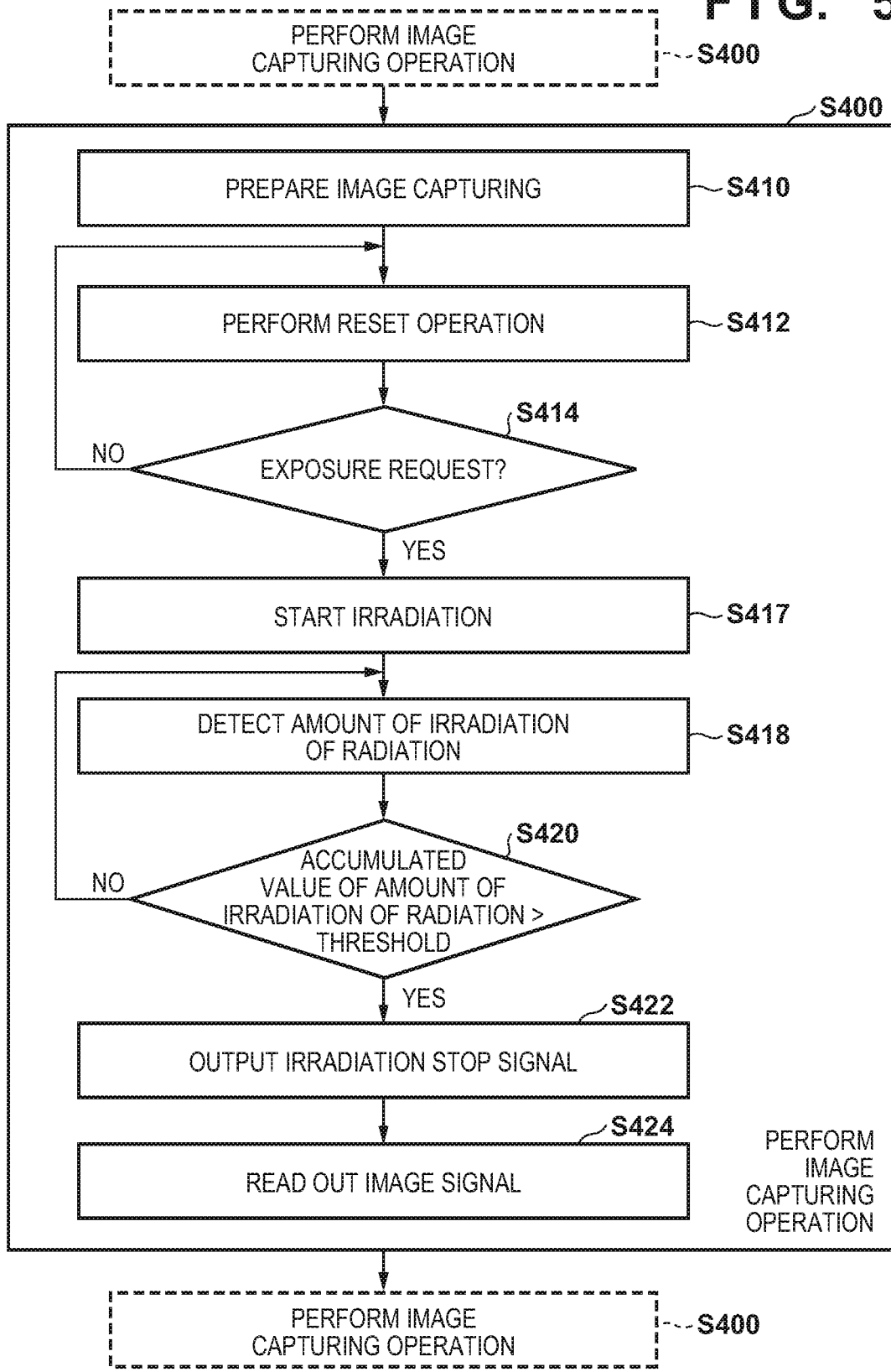
FIG. 5 is a flowchart showing a driving method in a comparative example of the radiation image capturing system in FIG. 1.

FIG. 5 is a flowchart showing a driving method in a comparative example for this embodiment of a radiation image capturing apparatus 210 and radiation image capturing system 200. The radiation image capturing apparatus may capture a still image by performing an image capturing operation of performing image capturing in step S400 once or may capture a moving image by performing step S400 repeatedly a plurality of times. A one-time image capturing operation in step S400 will be described here.

First, in step S410, an image capturing preparation is made. The image capturing preparation can include, for example, the setting of an image capturing portion, the setting of a radiation irradiation condition, the setting of a region of interest or exposure information for performing Automatic Exposure Control (AEC), and the like. They can be set, for example, by a user via an input device of a computer 240. The setting of the exposure information may be the setting of a target exposure amount in one region of interest. Alternatively, the setting of the exposure information may be a maximum value or an average value of exposure amounts in a plurality of regions of interest. Alternatively, the setting of the exposure information may be a difference between or the ratio of the maximum value and a minimum value of the exposure amounts in the plurality of regions of interest. Alternatively, the setting of the exposure information may be decided based on the image capturing portion or the radiation irradiation condition (irradiation energy). In accordance with the setting of the exposure information, a threshold of the amount of irradiation of radiation for deciding a timing at which radiation emission is to be stopped by a radiation source 230 in the processor 214 is decided.

After the image capturing preparation, the process shifts to step S412. In step S412, the processor 214 resets an image capturing unit 212 repeatedly until radiation irradiation from the radiation source 230 to the radiation image capturing apparatus 210 via an object is started. More specifically, the processor 214 causes each of a driver 114 and a readout unit 113 of the image capturing unit 212 to perform a reset operation of resetting respective pixels PIX repeatedly. In step S414, it is determined whether an exposure request from the user is input. If it is determined that radiation irradiation is started by the input of the exposure request, the reset operation is ended, and the process advances to step S417. If it is determined that radiation emission is not started without receiving an irradiation request, the process returns to step S412. In the reset operation, the driver 114 sequentially drives driving signals Vg supplied to gate lines G1, GA, G2, GB, G3, GC, and G4 of a pixel array 112 at an active level and removes dark charges accumulated in respective conversion elements C. In the reset operation, a reset pulse at the active level is supplied to a reset switch of an integration amplifier 105, resetting column signal lines Sig to a reference potential. In this specification, the dark charges refer to charges owing to, for example, a dark current or the like which are generated even though no radiation enters the conversion elements C.

Then, when the user turns on an exposure switch, the process advances to step S417. Based on, for example, a start notification supplied from an irradiation controller 220 via the computer 240, the processor 214 can recognize the start of radiation emission from the radiation source 230. A detection circuit that detects a current flowing through a bias line Bs, the column signal lines Sig, or the like of the pixel array 112 by the start of radiation irradiation. The processor 214 can recognize the start of radiation emission from the radiation source 230 based on an output of the detection circuit. Upon recognizing the start of radiation emission from the radiation source 230, the image capturing operation advances from step S417 to step S418.

In step S418, the readout unit 113 electrically connects, on a row-by-row basis, respective switches SW of detection elements 121 to 123 each for detecting the amount of irradiation of radiation out of the plurality of pixels PIX that form the pixel array 112. More specifically, the driver 114 sequentially drives driving signals VgA to VgC supplied to the gate lines GA to GC of the pixel array 112 at the active level. When the driving signals VgA to VgC are set at the active level, the respective switches SW of the detection elements 121 to 123 are electrically connected and turned on sequentially. Consequently, charges accumulated in the conversion elements C by radiation irradiation are read out to the readout unit 113 via the column signal lines Sig. Note that an order in which the switches SW are turned on may be set in accordance with a region of interest. The switches SW may be turned on, for example, sequentially from a detection element set at the edge of a radiation detection panel. For example, a readout operation for detecting the amount of irradiation of radiation that sets the driving signals VgA, VgB, and VgC at the active level in the order of the gate lines GA→GB→GC and reads out signals repeatedly in the order of the detection elements 121, 122, and 123 is performed.

In step S420, if an accumulated value of the amount of irradiation of radiation detected from each of the detection elements 121 to 123 is smaller than a threshold of a radiation dose preset in accordance with the setting of the exposure information, step S418 is repeated. In step S420, if the accumulated value of the amount of irradiation of radiation exceeds the threshold of the radiation dose preset in accordance with the setting of the exposure information, the process advances to step S422 in which the processor 214 outputs an irradiation stop signal for stopping radiation irradiation. The irradiation stop signal is supplied to the irradiation controller 220, and the irradiation controller 220 sends an irradiation stop instruction to the radiation source 230 in accordance with the irradiation stop signal. When radiation irradiation stops, the process advances to step S424 in which the processor 214 reads out charges generated by radiation irradiation from the respective pixels PIX in order to generate radiation image data.

Figure 6:
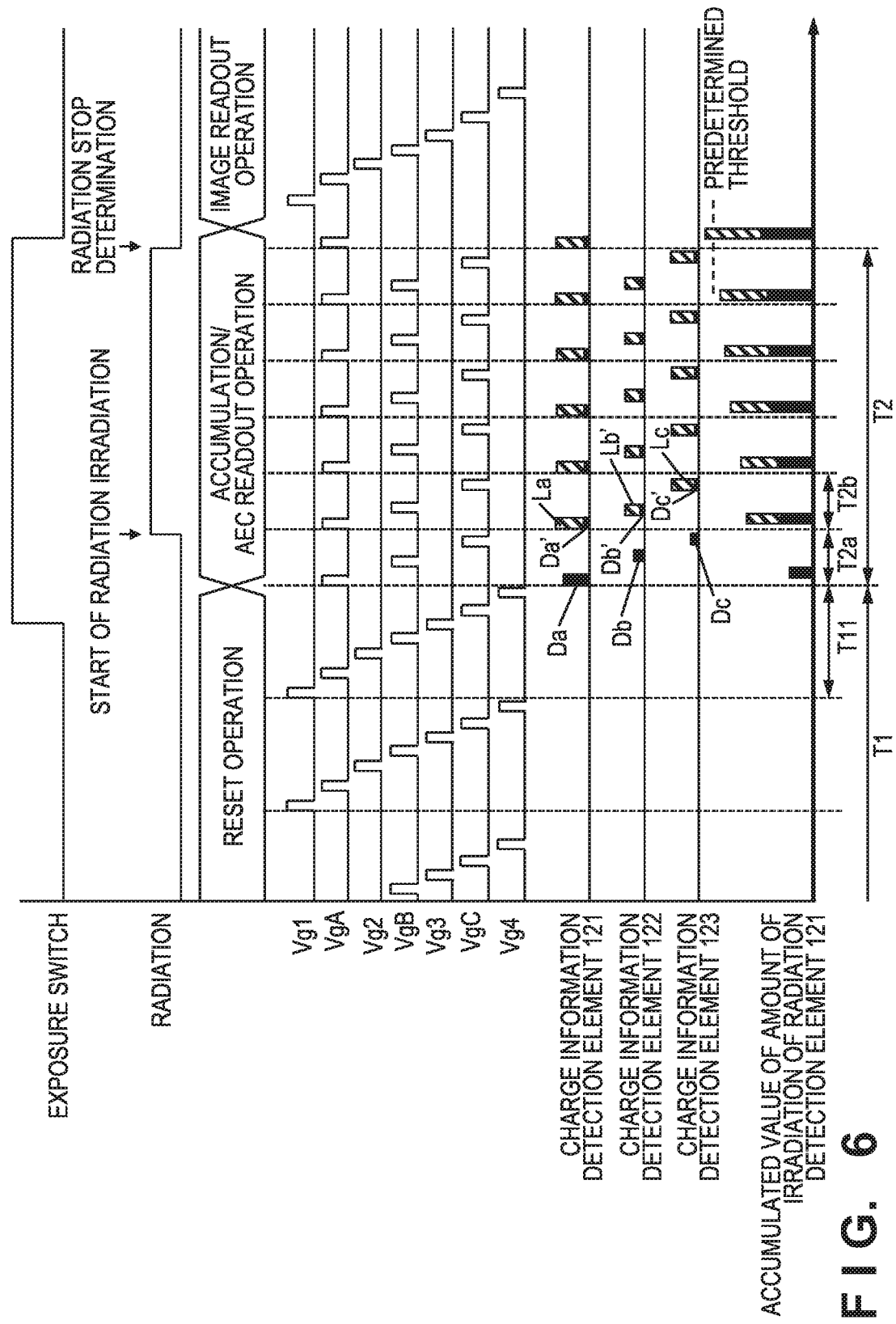
FIG. 6 is a timing chart showing a driving method in a comparative example of the radiation image capturing system in FIG. 1.

In order to clarify the usefulness of a radiation image capturing apparatus 210 and radiation image capturing system 200 of this embodiment, a comparative example will be described next with reference to FIG. 6. FIG. 6 is a timing chart showing a driving method in the comparative example for a driving method of the radiation image capturing apparatus 210. FIG. 6 shows, in respective driving states from step S412 to step S424, driving signals Vg applied to gate lines G and charge information as the amount of charges read out from each of detection elements 121 to 123.

FIG. 6 also shows an accumulated value of the amount of irradiation of incident radiation obtained from the charge information of the detection element 121 out of the detection elements 121 to 123.

If the driving signals Vg are at HI level, the switches SW of respective pixels PIX are electrically connected and turned on. In step S412, the pixels PIX and detection elements 121 to 123 of an image capturing unit 212 sequentially perform, for each row, a reset operation of repeating resetting. Then, consider a case in which the process shifts to driving for exposure control by an exposure request signal by operating an exposure switch by a user. Driving for the exposure control here refers to a readout operation for detecting the amount of irradiation of radiation that reads out the signal from each of the detection elements 121 to 123 repeatedly on a row-by-row basis for Automatic Exposure Control (AEC). When an exposure request is input by turning on the exposure switch, as in a period T2, the switches SW of the detection elements 121 to 123 are electrically connected (turned on) by setting driving signals VgA, VgB, and VgC at HI level sequentially. Moreover, a readout unit 113 is driven simultaneously, obtaining pieces of charge information A to C. These pieces of charge information include signal components La to Lc converted from radiation into light and generated by conversion elements C, and dark charge components Da to Dc and Da' to Dc' of the conversion elements C which are not needed for the operation of the amount of irradiation of incident radiation.

Further focusing on the dark charge components, the amount of the dark charge component Da read out in a period T2a and the amount of the dark charge component Da' read out in a period T2b are different. In a reset operation performed in a period T1, let T11 be a time from the start of one-time resetting to the start of next resetting by each of all the pixels PIX and the detection elements 121 to 123. On the other hand, let T12 be a time from the start of a readout to the start of a next readout in each of the detection elements 121 to 123 upon radiation irradiation by the exposure request. In the period T2, only rows where the selected detection elements 121 to 123 are arranged are driven at a high speed, and thus the time T11 the time T12 holds. In this case, for example, a time from the start of last resetting in a reset operation by the switches SW of a gate line GA to the start of the first signal readout in a readout operation and a time to the start of the second or subsequent signal readout in the readout operation are different. Accordingly, the amount of the dark charge component Da accumulated from the last resetting to the first signal readout and the amount of the dark charge component Da' accumulated until the second or subsequent signal readout are different, and thus the amount of the dark charge component Da the amount of the dark charge component Da' holds. Therefore, if, for example, the dark charge components are read out in the period T2a immediately before exposure, and the dark charge components are subtracted from the charge information read out in the period T2b for correction, the charge components generated by radiation irradiation may also be lost. Because the amounts of the dark charge components Da to Dc are different, for example, if a different detection element out of the detection elements 121 to 123 is selected each time a radiation image is captured, the amount of irradiation of radiation that is actually emitted may vary.

Figure 7:
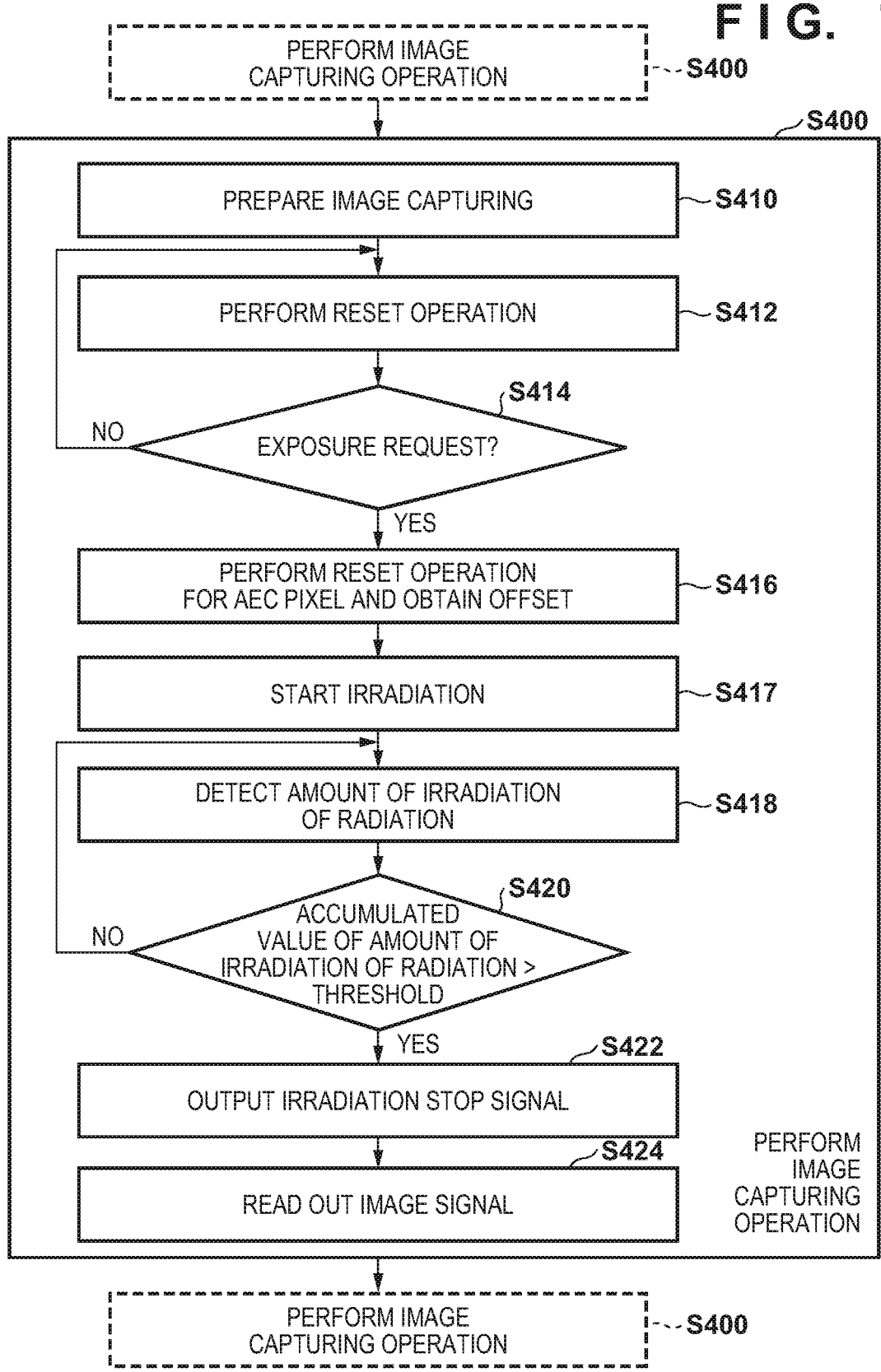
FIG. 7 is a flowchart showing a driving method of the radiation image capturing system in FIG. 1.
Figure 8:
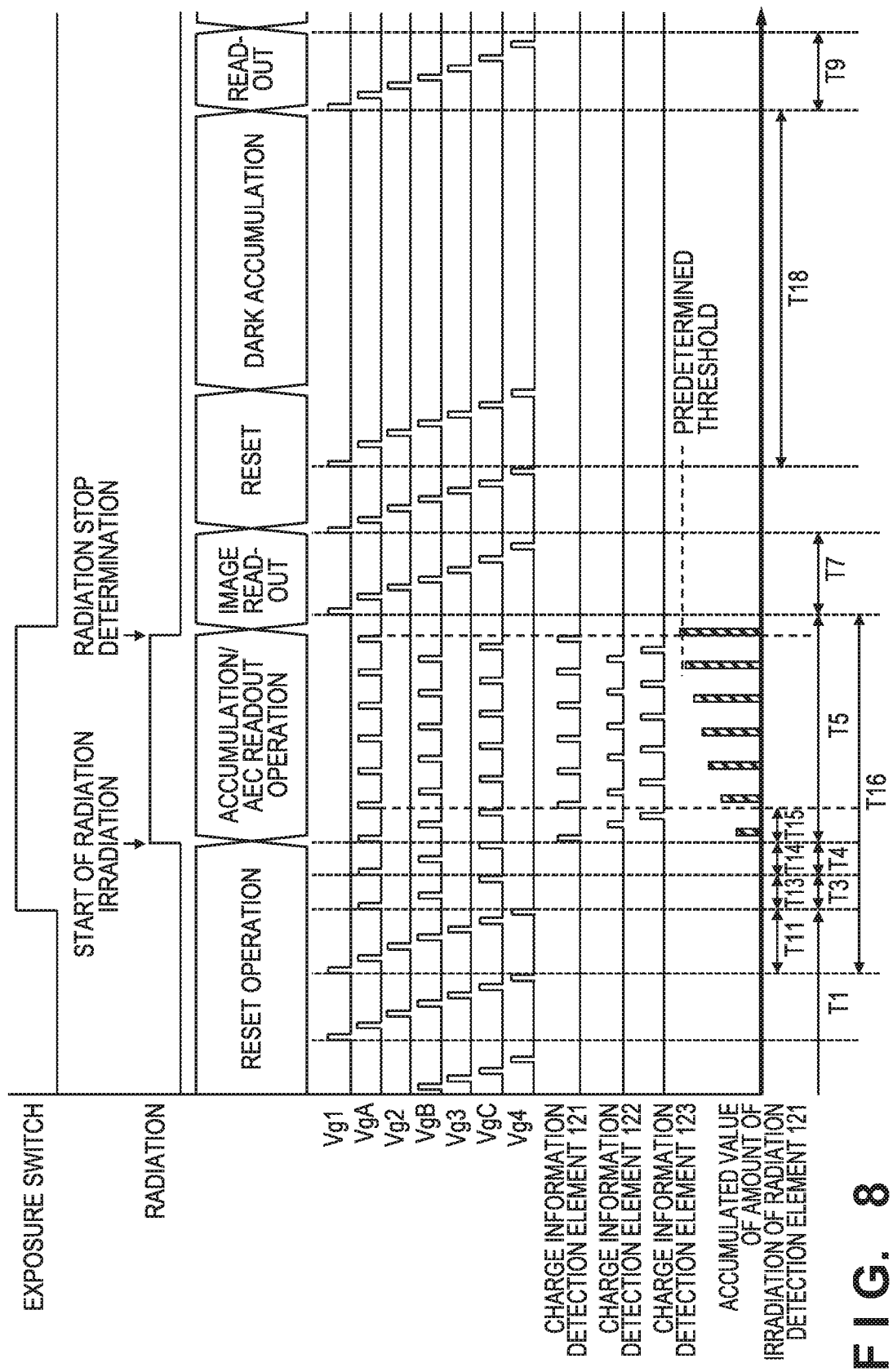
FIG. 8 is a timing chart showing the driving method of the radiation image capturing system in FIG. 1.

In order to suppress the influence of the dark charge components Da to Dc and Da' to Dc' as described above, a driving method of the radiation image capturing apparatus 210 and radiation image capturing system 200 in this embodiment will be described with reference to FIGS. 7 and 8. FIG. 7 and FIG. 8 are, respectively, a flowchart and timing chart showing the driving method of the radiation image capturing apparatus 210 and radiation image capturing system 200. In the flowchart of FIG. 7, step S412 and step S414 are the same as in FIG. 5 described above, and thus a description thereof will be omitted. In this embodiment, when an exposure request from the user is input, the process advances to step S416 before step S417 in which radiation irradiation is started. In step S416, in a period T3, a reset operation of resetting the detection elements 121 to 123 connected to the gate lines GA to GC is performed in accordance with the exposure request. The reset operation is controlled such that all the detection elements 121 to 123 are reset at least once. At this time, the pixels PIX except the detection elements 121 to 123 are not reset, setting a state capable of accumulating charges generated by incident radiation. Furthermore, after the reset operation, before a readout operation for detecting the amount of irradiation of incident radiation, in a time between the exposure request and radiation irradiation, the dark charge components used to correct the charge information may be read out. In other words, after reading out the dark charge components, the irradiation controller 220 may supply an irradiation instruction to the radiation source 230. In an arrangement shown in FIG. 8, the reset operation of the detection elements 121 to 123 is performed in the period T3, and a readout operation of reading out the dark charge components is performed in a period T4. After performing the readout operation of reading out the dark charge components in the period T4, the processor 214 shifts to step S418 in which a readout operation of reading out the amount of irradiation of incident radiation from each of the detection elements 121 to 123 is performed. In accordance with the start of step S418 in which the amount of irradiation of radiation is detected, the irradiation controller 220 supplies the irradiation instruction to the radiation source 230, irradiating the radiation image capturing apparatus 210 with radiation. At this time, in each of the detection elements 121 to 123, a time T13 from the start of resetting to the start of the readout of the dark charge component and a time T14 from the start of the readout of the dark charge component to the start of the first readout for detecting the amount of irradiation may be equal to each other. Furthermore, these times T13 and T14, and a time T15 from the start of one-time signal readout to the next readout in the readout operation of reading out the amount of irradiation of the incident radiation in each of the detection elements 121 to 123 may be equal to each other. In other words, a time needed for a reset operation of resetting each of all the pixels of the detection elements 121 to 123 once and a time in which a signal is read out from each of all the pixels of the detection elements 121 to 123 once may be equal to each other. Because only the rows where the selected detection elements 121 to 123 are arranged are driven at a high speed in the times T13, T14, and T15, the time T11 as a cycle in which all the pixels PIX and the detection elements 121 to 123 are reset can be equal to or longer than the times T13, T14, and T15. That is, the time T11≥the time T13=the time T14=the time T15 can hold in the times T11, T13, T14, and T15.

Detection pixels are reset before detecting the amount of irradiation of radiation from each of the detection elements 121 to 123. This makes it possible to reduce a difference in dark charge component owing to a time difference between the time T11 needed to reset each of all the pixels PIX and the detection elements 121 to 123 once, and the time T13 needed to reset each of the detection elements 121 to 123 once. This makes it possible to improve accuracy in detecting the amount of irradiation of incident radiation. In the period T4, it is also possible to obtain dark charge components for correcting the amounts of the dark charge component Da' to Dc' superimposed when dose information is obtained in a period T5. By detecting the amount of irradiation of the incident radiation based on charge information as a signal obtained in the period T5 and the amounts of the dark charge components as signals obtained in the period T4, it becomes possible to further improve the accuracy of the detected amount of irradiation.

Note that if the reset operation of the detection elements 121 to 123 is repeated a plurality of times in the period T3 in step S416, the operation may be repeated in the time T13. Similarly to the reset operation, if the readout of the dark charge components is repeated a plurality of times in the period T4, the readout may be repeated in the time T14, and obtained dark charge components may be averaged and used for data for correcting the dark charge components. Note that in this embodiment, each of the detection elements 121 to 123 is reset once in the time between the exposure request from the user and radiation irradiation, making the length of the period T3 in which the reset operation is performed equal to that of the time T13. Similarly, the dark charge component is read out from each of the detection elements 121 to 123 once, making the length of the period T4 in which the readout operation of the dark charge components is performed become equal to that of the time T14.

Next, in step S418, the processor 214 calculates the accumulated value of the amount of irradiation of the incident radiation from the charge information as the signal output from each of the detection elements 121 to 123. At this time, a signal input to the processor 214 may include an offset variation or a gain variation in the pixel array 112 and readout unit 113. To cope with this, offset correction or gain correction may be performed for each column signal line Sig before integrating signals output from the detection elements 121 to 123. This makes it possible perform higher-accuracy exposure control.

Then, in step S420, the processor 214 determines whether to stop radiation irradiation based on the accumulated value of the detected amount of irradiation of radiation. More specifically, the processor 214 determines whether the accumulated value of the amount of irradiation exceeds a preset threshold, and the process shifts to step S422 if the processor 214 determines that the accumulated value exceeds the threshold. In step S422, the processor 214 outputs an irradiation stop signal for stopping radiation emission from the radiation source 230. In accordance with this irradiation stop signal, the irradiation controller 220 sends a stop instruction to the radiation source 230, and the radiation source 230 stops radiation emission in accordance with the stop instruction. Consequently, an exposure amount is controlled properly.

When the radiation irradiation is stopped, the process advances to step S424 in which a readout operation of reading out an image signal for generating a radiation image from each pixel PIX arranged in the image capturing unit 212 is performed. In step S424, the processor 214 causes each of the driver 114 and the readout unit 113 to perform the readout operation. In the readout operation for the image signals, the driver 114 sequentially drives the driving signals Vg supplied to the respective gate lines G of the pixel array 112 at the active level. Then, the readout unit 113 reads out the charges accumulated in the conversion elements C via the plurality of column signal lines Sig and outputs them as radiation image data to the computer 240 via the multiplexer 108, the buffer 109, and the AD convertor 110.

Step S424 in which the image signals are read out may include driving for correcting offset components such as dark charges included in the image signals. For example, as in the arrangement shown in FIG. 8, after image signals are read out in a period T7, a reset operation of resetting the respective pixels PIX is performed. This reset operation may be performed on all the pixels PIX and the detection elements 121 to 123. A time in which all the pixels PIX and the detection elements 121 to 123 are reset may be equal to the time T11. Subsequently, during a period T18, offset components of the pixels PIX are accumulated and read out from the respective pixels PIX in a period T9. While the image signals read out in the period T7 include signals and offset components generated by radiation irradiation, data read out in the period T9 includes only offset components. Therefore, based on both the signals obtained in the period T7 and signals obtained in the period T9, a signal for generating a radiation image is obtained. More specifically, correction is performed by subtracting the signals obtained in the period T9 from the signals obtained in the period T7. Note that let T16 be a time from the start of the last resetting in the reset operation for the pixels PIX and the detection elements 121 to 123 shown in the period T1 to the start of a signal readout in the readout operation for reading out the image signals. In addition, let T18 be a time from the start of the last resetting in the reset operation performed after the readout operation for the image signals to the start of a signal readout in the readout operation for the offset components. The time T16 and the time T18 may be made equal to each other in order to correct the offset components of the pixels PIX more accurately.

Next, a method of reducing the influence of a potential change for each column signal line Sig owing to capacitive coupling between the column signal line Sig and a corresponding one of the conversion elements C when the signal is read out from each of the detection elements 121 to 123 in step S418 will be described with reference to FIG. 9. FIG. 9 is a timing chart showing a modification of the timing chart shown in FIG. 8. As in the timing chart described in FIG. 8 above, in accordance with an exposure request from the user, the reset operation of the detection elements 121 to 123 is performed in the period T3, and the readout operation of reading out the dark charge components is performed in the period T4. Subsequently, when radiation exposure is started, crosstalk serving as a noise component that changes the potential of the column signal line Sig even though the corresponding switch SW is not turned on (electrically connected) occurs by the capacitive coupling between the column signal line Sig and the conversion element C. Similarly to a dark charge component, a crosstalk component is not needed when integrating an accumulated value of the dose of incident radiation, requiring correction. This crosstalk component is generated regardless of whether the switch SW is ON or OFF. Therefore, in addition to the readout operation of reading out the signal from the column signal line Sig with the readout unit 113 by turning on the switch SW of each of the detection elements 121 to 123, the signal is read out from the column signal line Sig by turning off the switch SW in each of the detection elements 121 to 123. That is, after the signals are read out from the detection elements 121 to 123 and before next signals are read out, the processor 214 performs a readout operation of reading out the noise components of the column signal lines Sig that transmit the signals output from the detection elements 121 to 123 to the readout unit 113. A signal read out by turning on the switch SW includes the amount of the dark charge component Da' and a crosstalk component Cta in addition to a signal La effective in obtaining dose information generated by radiation. On the other hand, a signal read out by turning off the switch SW includes only Cta. In order to extract only the signal La, the amount of the dark charge component Da' read out before radiation irradiation and the crosstalk component Cta obtained when turning off the switch SW can be subtracted from the signal read out by turning on the switch SW. That is, by obtaining the dose information based on the signals obtained in the readout operation in the period T5, the signals by the dark charge components obtained in the period T4, and the crosstalk components serving as the noise components, it becomes possible to further improve the accuracy of radiation dose information.

In the arrangement shown in each of FIGS. 8 and 9, a method of performing the reset operations for the detection elements 121 to 123 and the readout operation of reading out data for correcting the dark charge components immediately before radiation irradiation has been shown. However, the present invention is not limited to this, and data for correcting the dark charge components of the detection elements 121 to 123 may be obtained in advance. In this case, the reset operation is performed first, and then the data for correcting the dark charge components is obtained. Also in this case, a time from the start of resetting in the reset operation to the start of the readout of the data for correcting the dark charge components and the time T15 as a cycle for detecting the dose of incident radiation are made equal to each other.

In this embodiment, the detection elements 121 to 123 each for detecting the amount of irradiation of radiation are selected among the plurality of pixels PIX arranged in the pixel array 112 of the image capturing unit 212 and used. However, a dedicated detection element different from the pixel PIX may be used in order to detect the amount of irradiation of radiation. Also in a case in which the dedicated detection element is used, a reset operation of resetting the respective detection elements repeatedly can be performed before the exposure request from the user is input. While the plurality of detection elements are reset sequentially, even if the exposure request is input halfway through a scan, an operation of resetting all the detection elements at least once in the period T3 is performed in accordance with the exposure request. After the reset operation is performed in the period T3, the amount of irradiation of incident radiation is detected. This makes it possible to make the amounts of the dark charge components output from the respective detection elements equal to each other as in the above description and improve the accuracy of the detected amount of irradiation. As in the above description, the period T4 in which the dark charge components are read out may be provided between the period T3 in which the reset operation is performed and the period T5 in which the amount of irradiation of radiation is detected. In the period T4, by obtaining a dark charge component for correcting a dark charge component superimposed when obtaining the dose information in the period T5, it is possible to improve the accuracy of the detected amount of irradiation of radiation.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. A radiation image capturing apparatus, comprising:
an image capturing unit comprising a plurality of pixels and configured to capture a radiation image, a part of the plurality of the pixels which is used as a detection element configured to detect radiation for obtaining an accumulated value of irradiated radiation incident on the radiation image capturing apparatus separately from obtaining the radiation image, and
a processor configured to calculate the accumulated value of irradiated radiation based on a signal from the part of the plurality of pixels, wherein the processor is configured to:
perform an operation of repeatedly resetting the plurality of the pixels before receiving an exposure request from a user;
perform a reset operation of resetting the part of the plurality of pixels in accordance with the exposure request, where pixels, of the plurality of the pixels, other than the part of the plurality of the pixels are not reset; and
calculate the accumulated value of irradiated radiation based on the signal from the part of the plurality of the pixels after the reset operation of resetting the part of the plurality of the pixels.

2. The radiation image capturing apparatus according to claim 1, wherein the image capturing unit comprises a pixel array where the plurality of pixels are arranged.

3. The radiation image capturing apparatus according to claim 1, wherein the radiation image capturing apparatus is configured to perform a first readout operation for calculating the accumulated value of irradiated radiation by repeatedly reading out the signal from the part of the plurality of the pixels, and
a time from a start of resetting in the reset operation to a start of a first signal readout in the first readout operation is the same as a time in the first readout operation from a start of a signal readout to a start of a next readout from the detection element.

4. The radiation image capturing apparatus according to claim 3, wherein a time in the operation of repeatedly resetting the plurality of the pixels from a start of resetting to a start of next resetting is not shorter than the time in the first readout operation from the start of the signal readout to the start of the next readout.

5. The radiation image capturing apparatus according to claim 4, wherein
   (i) the radiation image capturing apparatus is configured to output an irradiation stop signal for causing radiation irradiation to stop based on the accumulated value of irradiation radiation, and after causing the first readout operation to stop,
   the radiation image capturing apparatus is configured to perform a third readout operation of reading out a signal from the image capturing unit,
   the radiation image capturing apparatus is configured to perform a reset operation of resetting the image capturing unit after the third readout operation, and
   the radiation image capturing apparatus is configured to perform a fourth readout operation of reading out a signal from the image capturing unit after the reset operation of resetting the image capturing unit,
   (ii) the radiation image is obtained based on the signal obtained by the third readout operation and the signal obtained by the fourth readout operation, and
   (iii) a time from a start of last resetting in the reset operation of repeatedly resetting the image capturing unit to a start of a signal readout in the third readout operation is the same as a time from a start of resetting in the reset operation of resetting the image capturing unit to a start of a signal readout in the fourth readout operation.

6. The radiation image capturing apparatus according to claim 1, wherein the radiation image capturing apparatus is configured to perform a second readout operation of reading out the signal from the part of the plurality of the pixels at a time after the reset operation, and between the exposure request and radiation irradiation,
   the radiation image capturing apparatus is configured to perform a first readout operation of detecting the amount of irradiated radiation by reading out the signal from the part of the plurality of pixels repeatedly after the second readout operation, and
   the radiation image capturing apparatus is configured to detect the amount of irradiated radiation based on the signal obtained by the first readout operation and the signal obtained by the second readout operation.

7. The radiation image capturing apparatus according to claim 6, wherein a time from a start of resetting in the reset operation to a start of a signal readout in the second readout operation, a time from the start of the signal readout in the second readout operation to a start of a first signal readout in the first readout operation, and a time from a start of a signal readout to a start of a next readout from the part of the plurality of the pixels in the first readout operation are equal to each other.

8. The radiation image capturing apparatus according to claim 6, wherein after the signal is read out from the part of the plurality of the pixels and before a next signal is read out in the first readout operation, the radiation image capturing apparatus is configured to:
   perform a third readout operation of reading out a noise component of a signal line that transmits the signal output from the part of the plurality of pixels, and
   detect the amount of irradiated radiation based on the signal obtained by the first readout operation, the signal obtained by the second readout operation, and the noise component.

9. The radiation image capturing apparatus according to claim 1, wherein an irradiation stop signal for causing radiation irradiation to stop is output based on a detected amount of irradiated radiation.

10. A radiation image capturing system, comprising:
    a radiation image capturing apparatus according to claim 9;
    a radiation source configured to perform radiation irradiation; and
    an irradiation controller configured to control radiation irradiation, wherein
    the irradiation controller is configured to cause the radiation source to perform radiation irradiation to the radiation image capturing apparatus in accordance with a start of detection of an amount of irradiation of radiation, and
    the irradiation controller is configured to cause radiation irradiation from the radiation source to the radiation image capturing apparatus to stop in accordance with the irradiation stop signal.

11. A radiation image capturing system, comprising:
    a radiation image capturing apparatus according to claim 1;
    a radiation source configured to perform radiation irradiation; and
    an irradiation controller configured to control radiation irradiation, wherein
    the irradiation controller causes the radiation source to perform radiation irradiation to the radiation image capturing apparatus in accordance with a start of detection of an amount of irradiation of radiation.

12. The radiation image capturing apparatus according to claim 1, wherein an irradiation stop signal for causing radiation to stop is output for an operation of automatic exposure control based on the accumulated value of irradiated radiation.

13. A method for controlling a radiation image capturing apparatus including an image capturing unit comprising a plurality of pixels and configured to capture a radiation image, a part of the plurality of the pixels which is used as a detection element configured to detect radiation for obtaining an accumulated value of irradiated radiation incident on the radiation image capturing apparatus separately from obtaining the radiation image, the method comprising the steps of:
   repeatedly resetting the plurality of the pixels before receiving an exposure request from a user;
   resetting the part of the plurality of the pixels in accordance with the exposure request where pixels, of the plurality of the pixels, other than the part of the plurality of the pixels are not reset; and
   calculating the accumulated value of radiation incident on the radiation image capturing apparatus based on a signal from the part of the plurality of the pixels after the resetting the part of the plurality of the pixels.

* * * * *